United States Patent [19]

Della Valle et al.

[11] Patent Number: 5,057,223

[45] Date of Patent: Oct. 15, 1991

[54] PURIFICATION OF NERVE GROWTH FACTOR ($\beta$ SUBUNIT) BY SUBUNIT EXCHANGE CHROMATOGRAPHY

[75] Inventors: Francesco Della Valle; Lanfranco Callegaro, both of Padova, Italy

[73] Assignee: Fidia, S.p.A., Abano Terme, Italy

[21] Appl. No.: 544,531

[22] Filed: Jun. 28, 1990

[30] Foreign Application Priority Data

Jul. 20, 1989 [IT] Italy ............................... 48212 A/89

[51] Int. Cl.$^5$ ............................................ B01D 15/08
[52] U.S. Cl. ..................................... 210/635; 210/656; 210/198.2; 210/502.1; 530/399; 530/413; 530/417
[58] Field of Search ............ 210/635, 656, 659, 198.2, 210/502.1; 530/399, 413, 417

[56] References Cited

U.S. PATENT DOCUMENTS 4,407,744 10/1983 Young ................................. 530/399

FOREIGN PATENT DOCUMENTS 0121338 10/1984 European Pat. Off. ............ 530/399

OTHER PUBLICATIONS

Bernd, "Association of $^{125}$I-Nerve Growth Factor with PC12", The Journal of Biological Chemistry, vol. 259, No. 24, Dec. 1984, pp. 15509-15516.
Chiancone et al., Journal of Chromatography, 376, pp. 343-348 (1986).
Antonini et al., Analytical Biochemistry, 95, pp. 89-96 (1979).
Carrea et al., FEBS Letters, 104, No. 2, pp. 393-395 (1979).
Levi-Montalcini et al., J. Exp. Zool. 116:321-352 (1951).
Varon et al., Biochemistry, 6, pp. 2202-2209 (1967).
Angeletti, Proc. Natl. Acad. Sci. USA 65:668-674 (1970).
Harper et al., Nature, vol. 279, pp. 160-162 (1979).
Goldstein et al., Neurochemical Research 3:175-183 (1978).
Walker et al., Life Sciences, vol. 26, pp. 195-200 (1980).
Varon, Discussions in Neuroscience, vol. II, No. 3, (1985), pp. 9-52.
Hefti et al., Neuroscience, vol. 14, pp. 55-68 (1985).
Scott et al., Nature, vol. 302, pp. 538-540 (1983).
Ullrich et al., Nature, vol. 303, pp. 821-825 (1983).
Axen et al., Nature, vol. 214, pp. 1302-1304 (1967).
Methods of Enzymology, vol. 44, Immobilized Enzymes, Klaus Mosbach Hallbook et al., Molecular & Cellular Biology, 8:452-456 (1988).

Primary Examiner—Ernest G. Therkorn
Attorney, Agent, or Firm—Birch, Stewart, Kolasch & Birch

[57] ABSTRACT

A process is disclosed for the purification of Nerve Growth Factor ($\beta$ subunit) by subunit exchange chromatography.

8 Claims, 5 Drawing Sheets

MWM
(kD)

PURIFICATION OF NERVE GROWTH FACTOR (β SUBUNIT) BY SUBUNIT EXCHANGE CHROMATOGRAPHY

SUMMARY OF THE INVENTION

The present invention is directed to a method of separating and purifying Nerve Growth Factor, β subunit (βNGF). More specifically βNGF is highly purified from other proteins by a subunit exchange chromatography method.

BACKGROUND OF THE INVENTION

Subunit exchange chromatography is a bioaffinity method that allows the purification of oligomeric and self-associating protein systems by means of their subunits immobilized on a solid matrix.

The method is based on the specificity of subunit recognition and exploits the observation that properly immobilized subunits retain the capacity to interact in a reversible and specific way with soluble subunits of the same or of homologous proteins. The experimental conditions that cause the establishment of a finite association-dissociation equilibrium in solution will promote the establishment also of a new equilibrium between immobilized and soluble subunits. The subunits will be exchanged between the liquid and the solid phase, and part of the protein that was initially in solution will be bound to the matrix. The amount of matrix-bound oligomer is a function of several parameters, i.e. concentrations of immobilized and soluble protein, and the association constants in solution and in the solid phase.

The possibility of shifting the subunit association-dissociation equilibrium by changing the experimental conditions enables one to achieve an effective purification of a self-associating or oligomeric protein in two simple steps. First, the protein is extracted, for example, from a tissue homogenate or the culture medium and bound to its highly purified subunits or subunits of homologous protein immobilized under conditions that favor binding. Second, the protein is dissociated by eluting under conditions that favor the dissociation, without destroying the biological activity of the eluted protein and the immobilized subunits. The immobilized subunits are regenerated and become ready for a new purification cycle after equilibration with the associating buffer. It is best to immobilize the protein under conditions that stabilize the subunit. In this way, coupling to the resin through residues that are located at or near the intersubunit contact regions is avoided and immobilized subunits that display minimal heterogenecity in their interaction with soluble subunits are generated. A variety of systems have been purified successfully by means of immobilized subunits of the same protein or of homogolous subunits of the same protein capable of forming a hybrid with the protein to be isolated.

Additional information about this chromatographic method is reported by Chiancone E; et al., J. Chromatography 376, 343–348 (1986), Antonini E. et al., Anal. Biochem. 95, 89–96 (979), Carrea G., FEBS Letters 104, 393–395 (1979).

The present invention utilizes the basic concepts of such subunit exchange chromatography, with important improvements to prepare highly purified BNGF.

BRIEF DESCRIPTION OF THE DRAWINGS

FIG. 2 shows the immunoreactivity of eluted material by immunoblot technique.

DETAILED DESCRIPTION OF THE INVENTION

Figure 1:
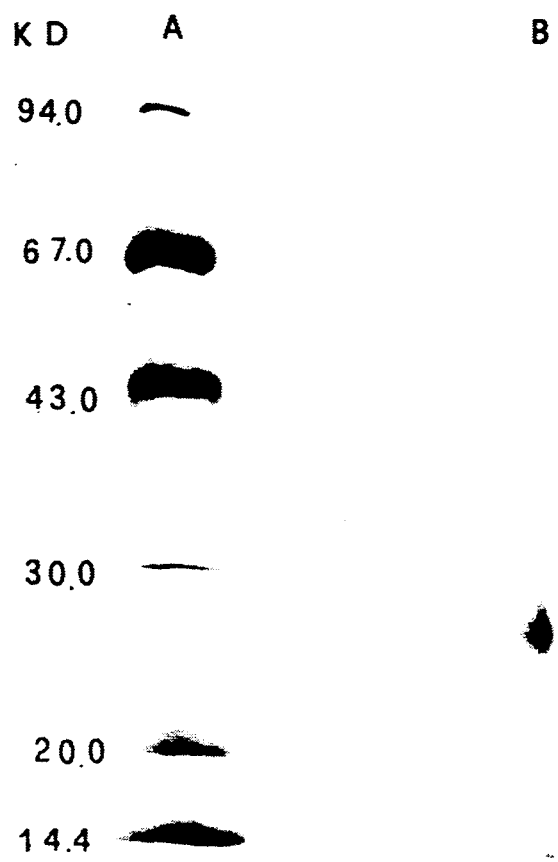
FIG. 1 shows the purity of eluted material as evaluated by SDS gel electrophoresis.

Nerve Growth Factor (NGF) was originally discovered in mouse sarcoma tumors (Levi-Montalcini R. et al., J. Exp. Zool. 116:321, 1951) and was then purified to homogeneity from submandibular salivary glands of male mice (Varon S. et al., Biochemistry 6:2202, 1967) and from snake venom (Angeletti R. H., Proc. Natl. Acad. Sci. USA 65:668, 1970). Many other relatively rich sources of NGF have also been reported, including guinea pig prostate (Harper G. P. et al., Nature 279:160, 1979) and human placenta (Goldstein L. D. et al., Neurochem. Res. 3:175, 1978, Walker P. et al., Life Science 26:195, 1980). Small quantities of NGF have been reported to be present in other tissues including the mammalian central nervous system (Varon S., Discussions in Neuroscience, Vol. II, No. 3, 1985; Hefti F. et al., Neuroscience 14:55, 1985). The physiological relationship between these potential sources of NGF and the apparent action sites is not very clear, but it is generally supposed that NGF is secreted by various peripheral tissues requiring innervation by those cells which respond to NGF.

The sequence and cloning of NGF obtained from submandibular glands of male mice were also carried out (Scott J. et al., Nature 302:538, 1983: Ulrich A. et al., Nature 303:821, 1983). The human NGF (β subunit) gene has also been successfully isolated and cloned (Ulrich A. et al., Nature 303:821, 1983: European Patent No. 0121388). NGF obtained from submandibular glands of mice is the type most completely characterized. NGF from mouse glands acts as a 7S proteic complex (molecular weight about 140,000 daltons) of three different subunits ($\alpha$, $\beta$, $\gamma$) including $Zn^+$. The activity of NGF is exclusively associated with the subunit $\beta$ (known as 2.5S NGF), it is a basic dimeric protein with a molecular weight of about 25,300 daltons (showing a molecular weight of about 12,650 daltons on electrophoresis with gel at high concentration of SDS), and has an isoelectric point of approximately 9.3. The amino acid sequences of βNGF from submandibular glands of male mice and human sources have been reported (Scott J. et al., Nature 302:538, 1983; Ulrich A. et al., Nature 303:821, 1983).

βNGF from mouse submandibular gland has been used for most of the studies on the activity of NGF in vitro and in vivo. The range of biological activity in vitro of βNGF has been determined both on primary neuronal cells and on clonal cells in cultures. The primary neuronal cells reported as responding to βNGF in vitro include fetal sensorial neurons (embryonic day 8–12) in dorsal root ganglia, autonomic noradrenergic fetal neurons in the sympathetic ganglia, cholinergic fetal neurons in the septum and adrenal chromaffin cells in development. While sensorial and sympathetic neurons depend on βNGF for survival and development, cholinergic neurons do not seem to require βNGF for survival, but only for their differentiation, that is to say, the expression of characteristic phenotypic traits bound to the neurotransmitter. The addition of βNGF to adrenal chromaffin cells (cells derived the neural crest) in the initial stage of their development causes the expression of neuronal phenotypes. The clonal cells reported as responding to βNGF in vitro include chromaffin adrenal cells derived from tumors of the neuronal crest known as pheochromocytoma cells (PC12) and human neuroblastoma cells. After treatment with βNGF these cells change from a highly proliferous form of behavior to a postmitotic neuronal state.

Since chick sympathetic and sensory neurons respond to mouse βNGF in vivo and in vitro and in a way similar to the corresponding mouse neurons, so that it is reasonable to conclude that the domain(s) of the βNGF molecule responsible for its biological activity must have been preserved, whereas other domains changed during evolution. This assumption was further substantiated when bovine βNGF was purified from bovine seminal plasma, and a detailed and comprehensive comparison between the biological activity of the mouse and bovine βNGF became possible. These experiments demonstrated that the biological activity of mouse and bovine βNGF were identical, although immunological crossreactivity was very limited. The same comparison was carried out between murine βNGF and human βNGF purified from human placenta. The molecular cloning of mouse, human, bovine, and chick βNGF together with amino acid sequence analysis of mouse βNGF has allowed comparison of the conserved and unconserved domains of these molecules and their relationship to biological activity and antigenicity. The overall conservation of βNGF during evolution is remarkably high. Of the 118 amino acids of mature mouse βNGF, only 16 amino acids are changed in bovine, 19 in chick βNGF, and 11 in human βNGF. As was expected from previous observations that the reduction of the three S—S bridges of mouse βNGF resulted in a complete loss of biological activity, all of the cysteine residues are strictly conserved in all the species. The apparent discrepancy between the overall high conservation of the amino acid sequence and the poor immunological crossreactivity is due to the fact that the amino acid changes between species are located in clusters. Hydropathy plots demonstrate that the changes are virtually exclusively located in the hydrophilic domains expected to be potential antigenic determinants. One single hydrophilic region has been shown to be strictly conserved in the NGF molecules of all species investigated so far.

The ability to isolate the gene of this molecule and to express them in other species raises two important possibilities. In principle it is now possible to produce this rare protein in quantity to study its structure and function or for possible pharmaceutical use. Mammalian cells are chosen in preference to bacteria for production only in those cases where the much cheaper microbial expression is not feasible. It is much less expensive to produce certain proteins in *E. coli* but, in general, this host/vector system faithfully reproduces only the linear sequence of amino acids which make up the protein, and this as an insoluble mass inside the bacterium. To the extent that a given product can be prepared from this material in a cost effective way, *E. coli* may be the preferred system, as in the case with certain smaller molecules, such as interferons, and some animal growth proteins where correct folding of the molecule in vitro is feasible. In cases involving generally proteins having only one disulfide bond, and with peptides or proteins whose use (diagnostic antigens or components of vaccines) does not require a particular conformation, these systems are excellent.

Therapeutic proteins, however, require correct conformation to be active and need a normal antigenic response. The further processing required may include glycosylation, formation of correct disulfide bonds, and other post-translational modification. *E coli* cannot do this. Mammalian cells and yeast can. The potential application of human NGF as a drug, obtained by biotechnological method, must consider these problems.

Fundamental ignorance of how the rare proteins fold impedes efforts at design and for this reason, the very meaning of authenticity as it applies to a recombinant-produced human βNGF can be elusive. If the protein is rare enough, the only material available in sufficient quantity for the evaluation may be recombinant-derived. Some problems correlated with the authenticity of the recombinant protein are discussed. For a protein with special characteristics (e.g. dimeric form, two or three disulfide bridge), the altered folding environment of the rDNA-derived products may compromise: i) the proper folding of the protein, ii) the proper pharmacokinetics behavior, and iii) secondary modifications. The possible functional consequences are: i) altered function (e.g. serum half-life, increased or decreased activity), ii) unanticipated function (e.g. immunogenicity, toxicity), and iii) no function.

The presence of three disulfide bonds in the correct conformation in the monomeric subunit of NGF involve a special characteristic for this protein in terms of biological activity and immunogenecity.

Evaluating the potential application of subunit exchange chromatography in the purification of protein, the no-covalent dimeric form of the biologically active form of the βNGF, the homology of βNGF form different mammalian sources, a chromatographic method has been developed for the purification of the biologically active form of the βNGF from different sources, using a subunit of the one specie covalently immobilized on a solid phase as solid support.

The present invention, therefore, in principle takes advantage of (1) the β subunit homology of the NGF from different sources; and (2) the no-covalent dimeric form of the βNGFs.

The process of the invention for the purification of the β subunit of a Nerve Growth Factor (NGF β subunit) comprises the following steps:

a) covalent binding a first NGF (β subunit) to a solid matrix;

b) combining the matrix having the first NGF (β subunit) immobilized thereon with a preparation to be purified and containing a second NGF (β subunit), whereby the second NGF (β subunit) is bound to said matrix;

c) eluting the matrix with a releasing agent to release the second NGF (β subunit) from the matrix; and d) recovering the released second NGF (β subunit).

As noted above, one of the principles which is utilized to advantage in the process of the invention is the β subunit homology of the NGF from different sources. Thus, the first NGF (β subunit) used in step (a) of the process can be any one of murine NGF, bovine NGF, human NGF from human placental tissue or human NGF from recombinant DNA technology and can be used to purify a preparation containing any one of the NGF molecules.

As a first step in the process, a first NGF ($\beta$ subunit) is bound to a solid matrix. This binding process can be performed according to per se known procedures, such as the standard activation method described in Axen R. et al., Nature 214, 1302–1304 (1967). Other methods of covalent immobilization are described in Methods of Enzymology, Vol. 44, Immobilized Enzymes, Mosbach Klaus. According to this type of procedure, a freeze-dried powder of the desired solid matrix is suspended in HCl, the gel swells immediately, and the swelled gel is washed with HCl. The ligand desired to be bound to the matrix is dissolved in a coupling buffer, and mixed with the gel, and stirred.

Excess ligand is washed away with coupling buffer and any remaining active groups are blocked with Tris-HCl buffer or with amino-containing compounds, such as glycine or ethanolamine. The product is then washed, preferably with three cycles of alternating pH.

The solid matrix to be used can be any known matrix, such as, for example, Sepharose ®.

Immobilized $\beta$ NGF can be utilized in batch procedures, in closed reactors or in a column for many purification cycles. The use of the batch procedures offers the advantage that the elution of the interacting protein is high when its concentration in solution is low, i.e. in the situation encountered usually during purification.

In order to improve the process in terms of yield of purified NGF ($\beta$ subunit), it is necessary to obtain a correct interaction between the blocked $\beta$-subunit and the $\beta$-subunit to be purified. Thus, it is important to measure the amount of protein (NGF) immobilized on the matrix (i.e. the coupling density of $\beta$NGF). Various per se known methods can be used to conduct the amino acid analysis. For example, the protein can be hydrolyzed in 6N HCl at 110° C. for 22 hours in vacuum-sealed tubes and the hydrolyzate analyzed on an analyzer, such as a JEOL Model JLC-6AH amino acid analyzer using single column methodology. To provide best results, the coupling density of $\beta$NGF to the matrix should be 0.01–1.0 mg, preferably 0.1–0.2 mg/ml of matrix.

The second major step of the process of the invention comprises combining the activated matrix (having a first $\beta$NGF immobilized thereon) with a preparation containing a second $\beta$NGF to be purified. After sufficient time for binding of the second $\beta$NGF to the matrix, the matrix is washed by stepwise using a saline buffered solution, preferably containing a denaturing-/releasing agent. The denaturing/releasing agent is used in this washing step at a concentration lower than that used in the following elution step.

After washing, the third major step of the process comprises eluting the matrix with a denaturing/releasing agent to release the second $\beta$NGF from the matrix. Since, as is clear to one skilled in the art, the purpose of the denaturing/releasing is to release the second $\beta$NGF, solid supports to be used in the process are selected which will first of all provide a support-protein covalent link, but which secondly are resistant to the denaturing agent so that the support cannot denature the protein.

Denaturing/releasing of the $\beta$NGF can be accomplished by the use of various denaturing agents which are capable of destroying the secondary and tertiary structures of the protein by the interaction with the amino acids of the protein sequence or by hydrating the microenvironment. Exemplary of such denaturing agents are guanidine hydrochloride, urea thiocyanate and magnesium chloride.

The following descriptions provide details of the manner in which the embodiments of the present invention may be made and used in order to achieve the separation, purification and concentration of $\beta$NGF to a degree of purity and biological activity not known heretofore. These descriptions, while exemplary of the present invention, should not be considered limitative of the invention and such variations which would be within the purview of one skilled in this art are to be considered to fall within the scope of this invention.

EXAMPLE 1

Murine Nerve Growth Factor ($\beta$ subunit) is bound to CNBr-activated Sepharose 4B by a standard activation method (Axen R. et al, Nature 214, 1302–1304, 1967). Glycine is added 6 hours later for quenching unreacted chemical groups. The matrix with the immobilized protein is washed exhaustively under conditions that favor dissociation of the protein from the matrix such as 0.1M glycine, pH 2.5; 4.5M MgCl, dissolved in 50 mM acetate buffer, pH 5.0; 6.0M guanidine hydrochloride dissolved in 10 mM phosphate buffer, pH 7.4. The resin is then washed with phosphate buffer and stored at 4° C. until used. The amount of protein immobilized on the matrix is determined by amino acid analysis of known volumes of settle Sepharose after hydrolysis with HCl (final concentration 6N) for 6 hours at 110° C. The coupling density of $\beta$NGF to Sepharose is between 0.01–1.0 mg, preferably 0.1–0.2 mg/ml of Sepharose.

Washed matrix with immobilized murine NGF ($\beta$ subunit) (i.e. 2 ml) is incubated with 3.0 mg of a protein solution containing murine Nerve Growth Factor ($\beta$ subunit) partially purified from submandibular salivary glands of male mice (Varon S. et al., Biochemistry 6, 2202, 1967) for 18 hours at 4° C. The unreacted biological material is washed out by 10 mM phosphate buffer, pH 7.4.

The matrix is washed by stepwise using a saline buffered solution containing the denaturing agent at a concentration lower than the one used in the purification process. Elution of the Nerve Growth Factor ($\beta$ subunit) is performed with a phosphate buffer containing a denaturing agent such as guanidine hydrochloride at a concentration of about 2.5–6.0M, preferably 4.0M, or urea at a concentration of about 6.0–10.0M, preferably 8.0M, or thiocyanate at a concentration of about 3.0–50M, preferably at 4.5M, or magnesium chloride at a concentration of about 3.5–5.0M, preferably at 4.0M, and dissolved at acidic condition. The eluted protein is dialyzed or desalted in a chromatographic column equilibrated with 50 mM acetate buffer, pH 5.5, 02M NaCl at 4° C. in order to eliminate the denaturing compound and stored at −80° C. until used.

Figure 2:
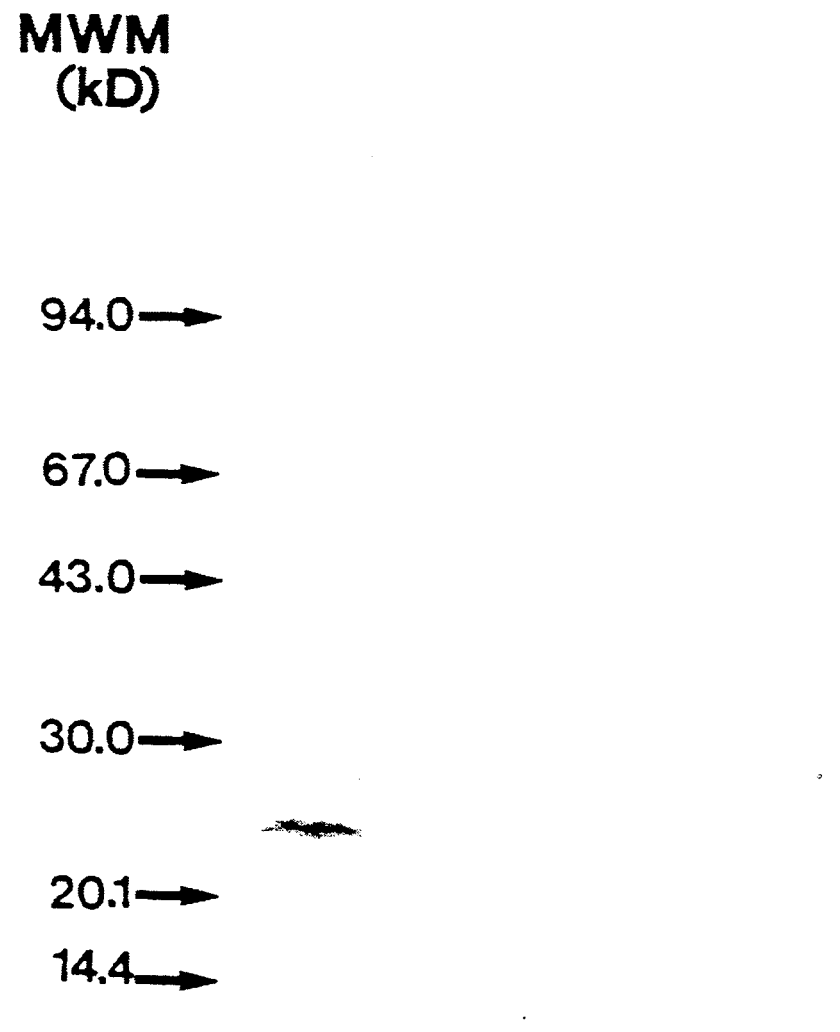
Figure 3:
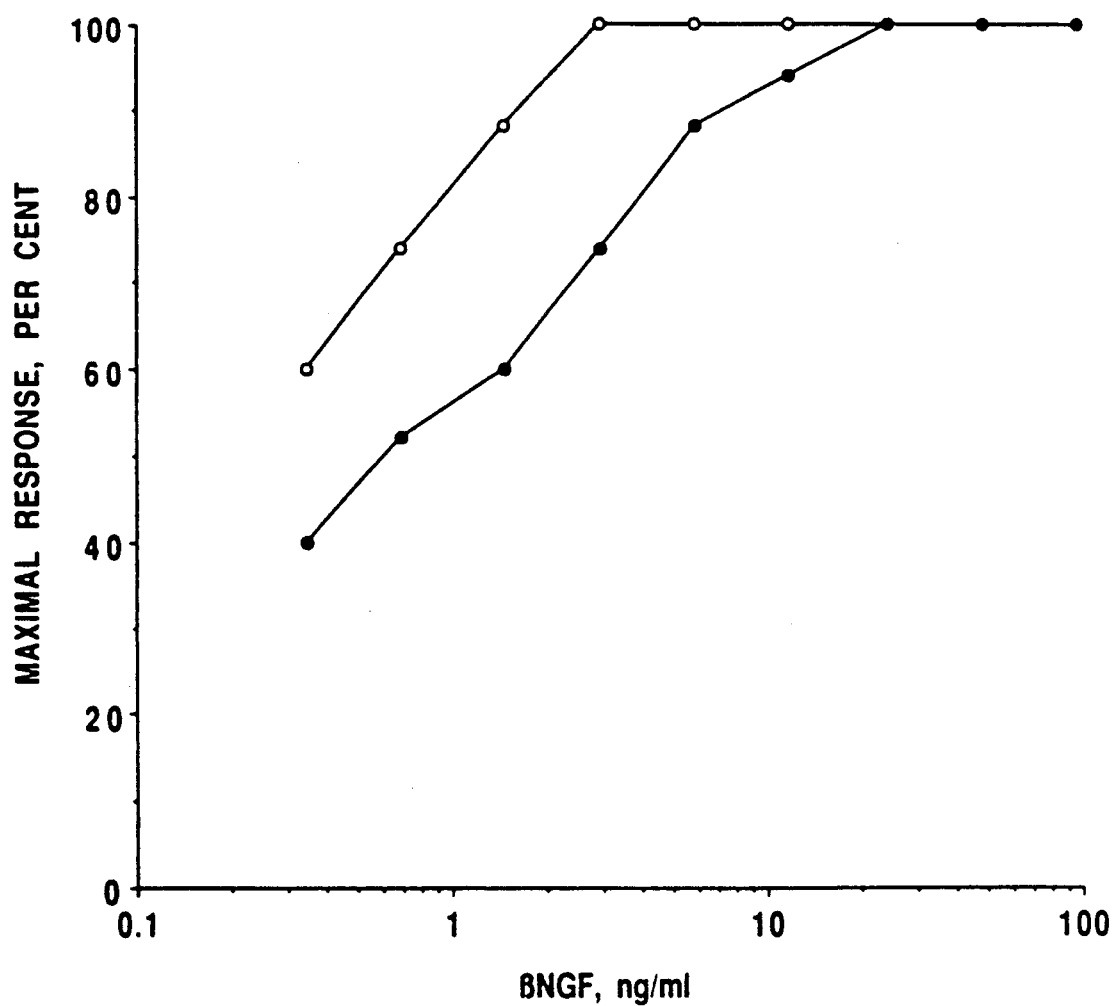
FIG. 3 shows the maintenance of the biological activity of the eluted material.

The purity of the eluted material is evaluated by SDS gel electrophoresis (FIG. 1) and the immunoreactivity by immunoblot technique (FIG. 2). The maintenance of the biological activity of the eluted material is checked utilizing dissociated fetal E8 chicken dorsal root ganglia cells (DRG-E8) (FIG. 3).

It may be noted that the immunoadsorbent column described above may be regenerated by treatment of the column with 20 bed volumes of phosphate buffer, pH 7.3, containing 0.1% NaN3.

EXAMPLE 2

Figure 4:
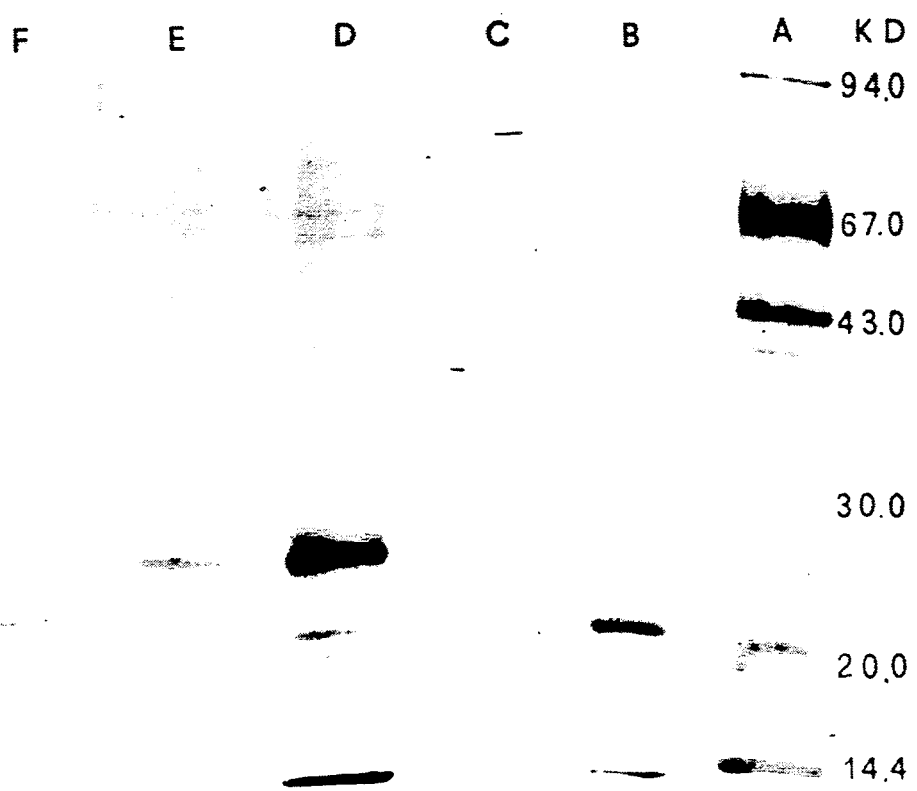
FIG. 4 shows the purity of bovine NGF(β subunit) as evaluated by SDS gel electrophoresis.
Figure 5:
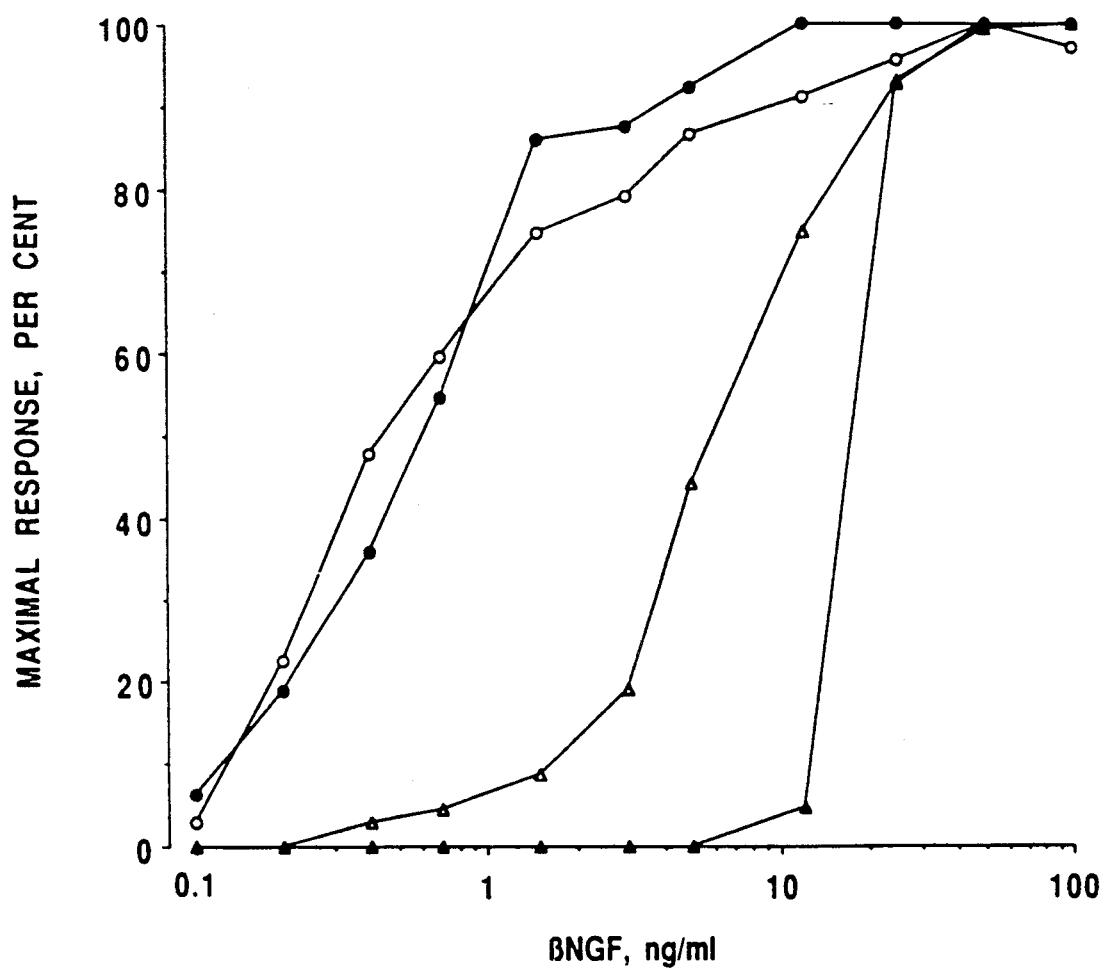
FIG. 5 shows the immunoreactivity of bovine NGF(β subunit) by immunoblot technique.

2 ml of the matrix with immobilized murine NGF (β subunit) is incubated with 2 mg of a protein solution containing partially purified bovine NGF (β subunit). The experimental procedures and the elution method are the same described in Example 1. The purity of bovine NGF (β subunit) eluted from the column is evaluated by SDS gel electrophoresis (FIG. 4), by immunoblot (FIG. 5). The maintenance of the biological activity of the eluted material is checked on DRG-E8. The identity of bovine βNGF is evaluated by the block of its biological activity on DRG-E8, utilizing antimurine affinity purified polyclonal antibodies mNGF (β subunit) as control in the same experiment.

EXAMPLE 3

2 ml of the matrix with immobilized murine NGF (β subunit) is incubated with 2 mg of a solution containing partially purified human NGF (β subunit) from human placental tissue (Goldstein L. D. et al., Neurochem. Res. 3, 175, 1978). The experimental conditions are the same as described in Example 1. The purity of the human NGF (β subunit), its identity and the biological activity of the eluted material are checked as described in Example 1. The identity of the human βNGF is carried out as described in Example 2.

EXAMPLE 4

The matrix with immobilized murine NGF (β subunit) is incubated with the culture medium, which contained recombinant human NGF (β subunit) (Hallbook et al., Molecular and Cellular Biology 8, 452, 1988). The experiments are carried out with the same procedures described in Example 1. Recombinant human NGF (β subunit) is eluted from the column using 4.0M guanidine hydrochloride, dissolved in 10 mM phosphate buffer, pH 7.4. The purity of the recombinant human NGF and the maintenance of the biological activity are evaluated as described in Example 1; the identity of recombinant human βNGF is checked with the methods described in Example 2.

EXAMPLE 5

The matrix with immobilized murine NGF (β subunit) is incubated with the culture medium which contained recombinant human NGF (β subunit) (Scott J. et al., Nature 302, 538, 1983; Ulrich A. et al. Nature 303, 821, 1983). The experiments are carried out with the same procedures described in Example 1. The biological active form of recombinant human NGF (β subunit) is eluted from the column using 4.0M guanidine hydrochloride, dissolved in phosphate buffer, pH 7.4. The purity of the recombinant human NGF, the maintenance of its biological activity, the identity of its form are checked with the materials and methods described in Example 1 and Example 2.

EXAMPLE 6

Highly purified bovine NGF (β subunit) is immobilized on the Sepharose 6B as previously described in Example 1. All the procedures, such as the evaluation of the quantity of immobilized protein and the stability of the chemical bond between solid support and protein, are carried out as described in Example 1. 2 ml of this matrix are incubated with human NGF (β subunit) as described in Example 3. Human NGF (β subunit) is eluted in the denaturing conditions described in the Example 3. The purity, the identity and the maintenance of its biological activity of the human NGF (β subunit) are evaluated with the materials and methods reported in Example 1 and Example 2.

EXAMPLE 7

The matrix with immobilized bovine NGF (β subunit is incubated with the culture medium, which contained recombinant human NGF (β subunit) (Hallbook et al., Molecular and Cellular Biology 8, 452, 1988). The experiments are carried out with the same procedures described in Example 1. Recombinant human NGF β subunit is eluted from the column using 4.0M guanidine hydrochloride, dissolved in phosphate buffer, pH 7.4. The purity of the recombinant human NGF, the maintenance of its biological activity, the identity of its form are checked with the methods and the materials described in Example 1 and Example 2.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for the purification of the β subunit of a Nerve Growth Factor which comprises:
    a) covalent binding a first β subunit of Nerve Growth Factor (NGF β subunit) to a solid matrix having a coupling density sufficient to achieve subunit exchange chromatography;
    b) combining the matrix having said first NGF (β subunit) immobilized thereon with a preparation containing a second β subunit of Nerve Growth Factor (NGF β subunit), whereby said second NGF (β subunit) is bound to said matrix;
    c) eluting said matrix with a releasing agent to release said second NGF (β subunit) from said matrix; and
    d) recovering said released second NGF (β subunit).

2. A method according to claim 1, wherein said first NGF (β subunit) is a murine NGF and said second NGF (β subunit) is a murine NGF, a bovine NGF, a human NGF prepared from human placental tissue or a human NGF prepared from recombinant DNA technology.

3. A method according to claim 1, wherein said first NGF (β subunit) is a bovine NGF, and said second NGF (β subunit) is a murine NGF, a bovine NGF, a human NGF prepared from human placental tissue or a human NGF prepared from recombinant DNA technology.

4. A method according to claim 1, wherein said first NGF (β subunit) is a human NGF prepared from human placental tissue, and said second NGF (β subunit) is a murine NGF, a bovine NGF, a human NGF prepared from human placental tissue or a human NGF prepared from recombinant DNA technology.

5. A method according to claim 1, wherein said first NGF (β subunit) is a human NGF prepared from recombinant DNA technology, and said second NGF (β subunit) is a murine NGF, a bovine NGF, a human NGF prepared from human placental tissue or a human NGF prepared from recombinant DNA technology.

6. A method according to any one of claims 1–5, wherein said releasing agent is guanidine hydrochloride, urea, thiocyanate or magnesium chloride.

7. A method according to any one of claims 1-5, wherein prior to said elution step said matrix having said second NGF (β subunit) bound thereto is washed to remove unreacted biological material.

8. A method according to claim 7, wherein said washing comprises stepwise washing with phosphate buffer, sodium chloride and a releasing agent selected from guanidine hydrochloride, urea, thiocyanate and magnesium chloride.

* * * * *